United States Patent [19]

Braun et al.

[11] Patent Number: 4,828,556

[45] Date of Patent: *May 9, 1989

[54] BREATHABLE, MULTILAYERED, CLOTHLIKE BARRIER

[75] Inventors: Ralph V. Braun, Roswell; Lance Garrett, Marietta; Robert J. Phelan, Woodstock; Richard S. Yeo, Dunwoody, all of Ga.

[73] Assignee: Kimberly-Clark Corporation, Neenah, Wis.

[*] Notice: The portion of the term of this patent subsequent to Dec. 15, 2004 has been disclaimed.

[21] Appl. No.: 925,332

[22] Filed: Oct. 31, 1986

[51] Int. Cl.$^4$ ............................................. A61F 13/16
[52] U.S. Cl. .................................... 604/365; 604/366; 428/913
[58] Field of Search ............... 604/365, 366, 370, 378, 604/381; 428/913; 128/156

[56] References Cited

U.S. PATENT DOCUMENTS

| | | | |
|---|---|---|---|
| 3,518,041 | 6/1970 | Brelich | 8/115.7 |
| 3,546,716 | 12/1970 | Laumann | 428/913 |
| 3,610,245 | 10/1971 | Bernardin et al. | 604/365 |
| 3,616,797 | 11/1972 | Champaigne | 604/365 |
| 3,654,928 | 4/1972 | Duchane | 604/365 |
| 3,808,165 | 4/1974 | Duchane | 604/365 |
| 3,934,587 | 1/1976 | Gordon | 428/913 |
| 3,952,347 | 4/1976 | Comerford et al. | 428/913 |
| 4,187,342 | 2/1980 | Holst et al. | 428/913 |
| 4,287,251 | 9/1981 | King et al. | 604/370 |
| 4,309,469 | 1/1982 | Varona | 428/913 |
| 4,392,861 | 7/1983 | Butterworth et al. | 604/366 |
| 4,425,126 | 1/1984 | Butterworth et al. | 604/366 |
| 4,603,077 | 7/1986 | Fujimoto et al. | 428/913 |
| 4,639,390 | 1/1987 | Shoji | 428/913 |
| 4,668,566 | 5/1987 | Braun | 604/320 |
| 4,713,068 | 12/1987 | Wang et al. | 604/366 |
| 4,713,069 | 12/1987 | Wang et al. | 604/378 |
| 4,753,834 | 6/1988 | Braun et al. | 604/378 |
| 4,758,239 | 7/1988 | Yeo et al. | 604/378 |

Primary Examiner—C. Fred Rosenbaum
Assistant Examiner—Sharon Rose
Attorney, Agent, or Firm—William E. Maycock

[57] ABSTRACT

A breathable, multilayer, clothlike barrier especially suitable for use as an outer cover or baffle in such disposable absorbent articles as diapers, sanitary napkins, and incontinent pads, which barrier has at least three layers:

A. a first layer which is a porous meltblown nonwoven web having a first side and a second side;

B. a second layer joined to the first side of the first layer, which second layer is a continuous film of a poly(vinyl alcohol), in which:

the film is not microporous in that it is substantially free of voids which connect the two surfaces of the film; and the film has an average thickness of from about 3 to about 250 microns; and C. a third layer joined to either the second layer or the second side of the first layer, which third layer is a porous nonwoven web;

wherein the first layer side of the second layer is intimately comingled with at least some of the fibers of the first side of the first layer, none of the pores at the surface of the first side of the first layer are so large as to significantly adversely affect the barrier properties of the barrier as a consequence of said comingling, and the barrier has a water vapor transmission rate at 37 degrees about fifty percent relative humidity of from about 100 to Celsius and about 5,000 g/m$^2$/24 hour and is impermeable to 0.9 percent by weight saline solution at about 21 degrees C. for a period of at least about one hour at a hydrostatic head of at least about 11.4 cm.

97 Claims, 3 Drawing Sheets

BREATHABLE, MULTILAYERED, CLOTHLIKE BARRIER

CROSS-REFERENCES TO RELATED APPLICATIONS

A breathable barrier which comprises a porous sheet coated with poly(vinyl alcohol) or laminated to a poly(vinyl alcohol) film is described and claimed in copending and commonly assigned application Ser. No. 06/926,033, entitled BREATHABLE BARRIER, filed of even date in the names of Richard S. Yeo and Daniel K. Schiffer. The use of a continuous film of poly(vinyl alcohol) joined to a porous substrate having a controlled structure is described and claimed in copending and commonly assigned application Ser. No. 06/925,425, now U.S. Pat. No. 4,713,068 entitled BREATHABLE CLOTHLIKE BARRIER HAVING CONTROLLED STRUCTURE DEFENSIVE LAYER, filed of even date in the names of Kenneth Y. Wang and Richard S. Yeo. Finally, a baffle for a sanitary pad having a central zone of reduced water vapor permeability, which zone can result from a continuous film of poly(vinyl alcohol) joined to the baffle material, is described and claimed in copending and commonly assigned application Ser. No. 06/925,446 now U.S. Pat. No. 4,713,069, entitled BAFFLE HAVING ZONED WATER VAPOR PERMEABILITY, filed of even date in the names of Kenneth Y. Wang and Richard S. Yeo.

BACKGROUND OF THE INVENTION

The present invention relates to a breathable, multilayered, clothlike barrier, i.e., a structure which is substantially impervious to liquid water but permeable by water vapor. More particularly, the present invention relates to a breathable, multilayered, clothlike barrier which is especially well suited for use as an outer cover or baffle in such absorbent articles as disposable diapers, sanitary napkins, and incontinent pads.

Absorbent articles, especially disposable absorbent articles such as diapers, sanitary napkins, bedpads, incontinent pads, and the like are well known and important items of commerce. Such articles are capable of absorbing and retaining liquid discharges from the body. They typically have an outer cover or baffle of a liquid-impermeable plastic film, such as a polyethylene or polypropylene film, to prevent leakage of retained liquid from the article and the soiling of items of clothing, bedding, furniture, and the like.

Such liquid-impermeable film prevents, or at least minimizes, leakage by establishing a barrier to the passage of liquid from the absorbent article in situations where either the capacity of the absorbent article has been exceeded or the loading of the target zone exceeded the capacity of the absorbent article to wick liquid from the target zone to storage areas.

Such film, however, suffers from several disadvantages. Because the film is impermeable to both liquid and water vapor, the absorbent article feels hot when dry and clammy when wet. Such clammy state can cause irritation of the skin and even severe dermatological problems, such as diaper rash on infants wearing disposable diapers which have been left on too long. In fact, diaper rash can develop relatively quickly because of illness or changes in diet. In addition, the plastic film employed as the outer cover is severely lacking in aesthetic qualities, especially for such products as disposable diapers.

One proposal for the elimination of such disadvantages is the use of a breathable, liquid impermeable barrier in the construction of the absorbent article, usually as an outer cover or baffle. As used herein, the term "breathable" means that the barrier is pervious to water vapor; that is, water vapor will pass through the barrier. While considerable progress has been made in the development of breathable films, such materials typically are lacking in aesthetic qualities.

Various breathable outer coverings or other materials are known. For example, U.S. Pat. No. 3,156,242 discloses a flexible absorbent sheet which is useful as a surgical dressing. The backing sheet or outer layer of the dressing is either air pervious by nature, such as a microporous film, or has had holes or slits formed in it. The example employed a perforated polyethylene film.

U.S. Pat. No. 3,426,754 teaches a breathable medical dressing. Such dressing comprises a backing having an open-celled structure, preferably coated with a continuous layer of a microporous pressure-sensitive adhesive. The backing employs a plastic film to which the desired properties have been imparted as a result of special processing conditions. The film typically can be prepared from polyolefins, polyacetals, polymethylene sulfide, polyethylene sulfide, polyphenylene oxide, polyamides, polyesters, and the like. The film possesses an open-celled structure, the voids of which are accessible to the outside surface by means of passageways which generally are under 5,000 Angstroms, e.g., from 100 to 5,000 Angstroms. In addition, such film has a final crystallinity of at least 40 percent.

A porous sheet and a process for making it are described in U.S. Pat. No. 4,347,844. The sheet is reported to be useful as a water-impermeable, vapor-permeable backing sheet for disposable diapers. The sheet contains a filler, the particles of which have been broken by the application of a compressive force to cause the formation of voids or spaces, i.e., micropores, which permit the passage of water vapor through the sheet while acting as a barrier to liquid water. The sheet apparently can be made of a nonfoamed thermoplastic resin, such as polyethylene and nylon. In addition, the patent suggests that the film can be a composite of a polyethylene or nylon film and spunbonded polyethylene or polyester. The use of a spunbonded material alone does not appear to be within the scope of the disclosure.

Another type of microporous film is described in U.K. Pat. No. GB 2,115,702B. The patent is directed toward an absorbent article, such as a disposable diaper or sanitary napkin, in which the article has a vapor-permeable, liquid-impermeable backing sheet. The backing sheet is composed of a film produced by mixing 100 parts by weight of a polyolefin resin, 28 to 200 parts by weight of a filler, and 10 to 70 parts by weight of a liquid or wax-like hydrocarbon polymer, molding the mixture to form a film, and then stretching the film laterally and/or longitudinally until it has a dimension of more than 1.2 times its original dimension in that direction, thereby resulting in the formation of fine pores in the film. Examples of polyolefins include polyethylene and polypropylene. A variety of fillers can be used, and examples of the hydrocarbon polymer include liquid polybutadienes, liquid polybutenes, and hydrogenates of liquid polybutadienes, among which saturated polyhydroxysubstituted hydrocarbons obtained by hydrogenating hydroxy-terminated liquid polybutadienes are preferred. See also U.S. Pat. No. 3,870,593 which describes stretching a film containing finely divided particles of a nonhygroscopic inorganic salt, such as calcium carbonate, in order to obtain a microporous film. The microporous sheet material described in U.S. Pat. No. 3,640,829 involves incorporating within the polymer an inorganic salt which is leached out to produce the micropores.

U.S. Pat. No. 4,591,523 relates to an apertured, macroscopically expanded, three-dimensional polymeric web exhibiting breathability and resistance to fluid transmission. The web is reported to have particular utility as a breathable barrier for a disposable diaper. The web preferably comprises a deeply drawn three-dimensional structure containing a multiplicity of debossments of macroscopic cross-section (i.e., visibly perceivable by the normal human eye at a perpendicular distance of about one foot), each of said debossments originating as an aperture in a first surface of the web and having a continuously interconnected side wall extending in the direction of a second, remotely located parallel surface of the web. The side wall of each debossment terminates to form an end wall in the second surface of the web. The end wall includes a multiplicity of apertures, each of said apertures being sized and shaped to independently support an aqueous fluid meniscus. These smaller apertures in each end wall are so spaced relative to all adjacent apertures in the end wall that the aqueous fluid menisci supported in the apertures do not contact one another.

Waterproof products capable of transmitting air and water vapor which have fabric-like aesthetic properties are described in U.S. Pat. No. 3,932,682. The products are made by spray-spinning filamentary material directly onto an open-celled microporous polymer film, such that thermal self-bonding occurs between the filamentary material and the film, or by spray-spinning the filamentary material in the same manner onto an elastic film, stretching the resulting product until an open-celled structure is produced in the film portion of the product and thereafter heating or heat setting the resulting product at substantially constant length to impart dimensional stability thereto. Polymers suitable for making the film appear to be those described in U.S. Pat. No. 3,426,754, discussed hereinabove. As already noted, the filamentary material is produced by spray-spinning, i.e., meltblowing, directly onto the film.

U.S. Pat. No. 4,308,303 describes a flocked, foam coated, fibrous-reinforced, water vapor permeable barrier having the appearance of fabric and capable of filtering bacteria. The barrier comprises a microporous polyolefin film coated on at least one surface with a foamed latex polymer, flocked fibers on the exterior surface of said foamed latex polymer, and a web of spunbonded fibers on the exterior surface of the flocked, foamed latex polymer. The film is rendered microporous by stretching a film which contains minute fracture sites or pore-nucleating agents such as finely divided filler and/or minute crystalline domains. The use of a finely divided, inorganic, water-insoluble, inert filler such as calcium carbonate having an average particle size of less than 3 microns is preferred.

U.S. Pat. No. 4,560,611 relates to a moisture permeable, waterproof coated fabric. Briefly, a microporous polyurethane layer is formed on a base fabric which may be knitted, woven, nonwoven, or the like. The coating solution consists of a polar organic solvent solution containing 8 to 25 percent by weight of a polyurethane elastomer, 0.1 to 10 percent by weight of a water repellent agent, 0.2 to 3 percent by weight of a polyisocyanate, and 1 to 8 percent by weight of a nonionic surfactant. The water repellent agent typically is a fluorine- or silicone-based material. The polyisocyanate usually will be any of the well known di- or triisocyanates. The polyurethane elastomer can be a polyester or polyether polyurethane.

A somewhat similar approach is described in European Patent Application No. 85308671.8, Publication No. 0 184 392 A2. A waterproof, moisture-vapor permeable unitary sheet material comprises a microporous polymeric matrix having pores comprising continuous passages extending through its thickness and opening into the opposite surfaces thereof, the passages being sufficiently filled with a moisture-vapor permeable, water-impermeable, hydrophilic material to prevent the passage of water and other liquids through the unitary sheet material while readily permitting moisture vapor transmission therethrough, thereby rendering the sheet material breathable. Preferably, the average pore size will be less than about 10 percent of the thickness of the matrix. By way of example, the average pore size for a matrix having a thickness of about 10 to 50 micrometers typically will be on the order of 1 to 5 micrometers or less. By contrast, the average pore size or opening of a woven fabric is about the same magnitude as its thickness. A matrix having too large a pore size will permit the passage of water therethrough as hydrophilic material solidified therein will not sufficiently close the pores against the passage of liquid. The matrix can be prepared by known methods from any polymeric material which is substantially impenetrable by water. Suitable polymeric materials include polyolefins, polyesters, polyamides, and the like. The preferred hydrophilic material is polyethylene oxide which preferably is polymerized with a polyisocyanate to give a polyurethane.

U.S. Pat. No. 4,197,371 discloses a water vapor absorbing and transmitting sheet material. The sheet material comprises a natural or synthetic rubber or a rubber-like polymer having uniformly incorporated therein particles of at least one swellable modified polymer. Examples of suitable swellable modified polymers include, among others, modified starches and celluloses. Apparently, such sheet materials are not suitable for use as an outer covering for a disposable absorbent product, e.g., a diaper or sanitary napkin. See also U.S. Pat. No. 4,178,271 which describes a similar sheet material based on a sheet-like structure of poly(vinyl chloride) or a copolymer of vinyl chloride.

U.S. Pat. No. 3,869,310 describes flexible sheet materials which are leather-like. Although the materials allegedly have improved physical properties, particular properties, such as water vapor permeability, are not discussed. The materials comprise a nonwoven fibrous mat and a polymeric impregnant which has a porous structure and is substantially not bonded to the fibers of the mat. The materials are obtained by preparing a nonwoven fibrous mat composed of fibers prepared from at least two different polymeric materials, impregnating the mat with a first liquid which is a solvent for one of the polymeric materials and a nonsolvent for the other polymeric materials, dissolving the fibers composed of the polymeric material which is soluble in the liquid, and coagulating the polymer solution resulting from the addition of the first liquid into a porous polymeric structure which is substantially not bonded to the undissolved fibers by the addition of a second liquid which is a nonsolvent for all of the polymeric materials originally present in the nonwoven fibrous mat but which is at least partially miscible with the first liquid. The list of suitable polymeric materials which can be employed includes poly(vinyl alcohol), although the preferred combinations of polymeric materials apparently are nylon-6 and polystyrene, nylon-6 and polypropylene, poly(ethylene terephthalate) and polystyrene, poly(vinyl chloride) and polypropylene, nylon-6 and poly(vinyl acetate), and nylon-6 and a polyurethane elastomer. One example, however, involved the use of a nonwoven mat composed of fibers of poly(vinyl chloride) and poly(vinyl alcohol); the first liquid was N,N-dimethylformamide which is a solvent for poly(vinyl alcohol) but a nonsolvent for poly(vinyl chloride).

The use of poly(vinyl alcohol) as a binder for a nonwoven fabric is described in U.S. Pat. No. 3,518,041. The nonwoven fabric is composed of cellulose fibers alone or in combination with other natural or synthetic fibers. The binder is a poly(vinyl alcohol) resin in film, powder, fiber, or other particulate form which is crosslinked in situ with formaldehyde. The binder is applied to the fabric as an aqueous solution or poly(vinyl alcohol) fibers may be incorporated into the fabric and activated by treating the fabric with water. The fabric then is treated with an aqueous solution of formaldehyde which contains a catalyst.

A disclosure somewhat similar to that of the above patent is found in U.S. Pat. No. 3,253,715 which describes boil-proof nonwoven filter media. The media are prepared by treating a multilayered nonwoven fabric with a binder which is an aqueous solution of poly(vinyl alcohol) and a polyacrylic acid or crosslinked polyacrylic acid.

It is interesting to note that, in contrast to U.S. Pat. Nos. 3,518,041 and 3,253,715, U.S. Pat. No. 3,590,585 describes a composite structure, useful as an artificial seaweed, which employs water-decomposable poly(vinyl alcohol) filaments to temporarily hold buoyant, water-resistant strands in place during the handling, transporting, and installing of the product. Also of interest in this regard is U.S. Pat. No. 4,304,812 which describes the backcoating of an open-weave fabric. Prior to the backcoating step, a temporary protective coating is applied to the face of the fabric. After backcoating the fabric, the protective coating is removed with a solvent medium. Suitable protective coatings preferably are at least partially water soluble and include water-soluble poly(vinyl alcohol) or partially hydrolyzed poly(vinyl acetate).

U.S. Pat. No. 3,597,307 describes a supple sheet material which is composed of a fibrous nonwoven web and a polyurethane filler. The fibers of the web can be prepared from poly(vinyl alcohol) and the amount of the filler can be up to 30 percent by weight, based on the weight of the sheet material. Although the sheet material is stated to have a good water vapor pick-up value, it is not known if the material is permeable to water vapor. See also U.S. Pat. No. 4,006,052.

U.S. Pat. No. 3,891,487 discloses a decorative laminate which has a textile backing, a crushed thermoset plastic foam bonded thereto, and a transparent polymeric film overlaying the foam. The film preferably is cast from a latex; suitable materials for preparing the latex include poly(vinyl alcohol). The film can be made breathable by mechanically foaming the latex before casting, mechanically puncturing the film, using chemical blowing agents, or dissolving or digesting out temporary fillers placed in the latex before it is cast. The textile backing apparently can be either woven or nonwoven. The decorative laminate is useful as, for example, a simulated oil painting, and clearly is not intended to be contacted by water.

Microporous coated fabrics are described in U.S. Pat. No. 4,226,906. Microporosity apparently results from the use of clustered microspheres. The microspheres may be synthetic or naturally occurring. If the former, they are prepared by bonding individual microspheres in a matrix which is insoluble in the coating composition; the bonding agent for such matrix can be, for example, poly(vinyl alcohol). However, the patent does not appear to teach the use of poly(vinyl alcohol) in the preparation of microporous coated fabrics when naturally occurring microspheres are used; in such case, the coating composition was based on poly(vinyl chloride) and the fabric was a nonwoven polyester.

U.S. Pat. No. 4,415,617 discloses a base fabric for the manufacture of embroidery and lace. The base fabric is a nonwoven web of poly(vinyl alcohol) fibers which has been processed in such a manner as to convert one surface of the web into a gas-permeable film comprising thermoplasticized and rehardened, flattened fibers and portions of fibers. The base fabric then can be dissolved away from embroidery stitched thereon by exposing the fabric to water at a temperature of about 100 degrees C.

U.S. Pat. No. 4,454,191 describes a waterproof and moisture-conducting fabric coated with a hydrophilic polymer. The fabric can be a woven, knit, felt, or nonwoven material which is composed of natural, synthetic, or mineral fibers. The fabric itself must be permeable to water vapor. The fabric is sealed with a hydrophilic polymer which is capable of absorbing, transporting, and releasing water molecules. Such capability results from the presence in the polymer of hydrophilic groups, such as hydroxy, amino, ether, and carboxy groups. Thus, suitable polymers include those prepared from hydroxyalkyl acrylates, the acrylic or methacrylic esters of polyalkylene oxides or polyalkylenimides, and the like. Other suitable polymers include modified vinyl alcohol resins, regenerated cellulose, a poly(vinyl chloride) having built-in monomers which have powerful hydrophilic groups, copolymerizates of vinyl chloride and vinyl acetate in which the acetate groups have been hydrolyzed to hydroxy groups, and polyurethanes having excess hydroxy or amino groups.

A somewhat related disclosure is found in German Published patent application No. 3417909 A1, which describes the use of a water-soluble poly(vinyl alcohol) film in the resorbent material of a sanitary pad. The film reportedly prevents soiling of clothing while permitting sanitary disposal of the used article. There appears to be no mention of the characteristics of the film or where and how the film is placed in the pad.

It perhaps should be mentioned that there is a large body of literature on the preparation of microporous films, only a relatively small portion of which has been discussed hereinabove. While a detailed discussion of such body of literature is beyond the scope of this section, a limited number of additional, representative references perhaps should be mentioned for the sake of completeness. Such references include, by way of illustration only, U.S. Pat. Nos. 4,247,498, 4,519,909, 4,257,997, 4,452,845, 4,539,256, 3,843,761, 3,679,538, 4,430,278, 4,289,832, 4,384,023, 4,472,328, 4,197,148, U.K. Published Patent Application No. GB 2,103,537A, Japanese Published Patent Application No. 57-142323, and European Patent Application Nos. 84307198.6, Publication No. 0 141 592 A2, and 83305161.8, Publication No. 0 105 629 A2.

Finally, a more aesthetically pleasing barrier is described in U.S. Pat. No. 4,578,069. The barrier is a breathable baffle composite which is employed in the construction of a sanitary napkin. The baffle is formed by joining webs of a meltblown polyolefin and a spunbonded polyolefin, with the latter providing a surface for the adhesive which permits attachment of the napkin to an article of clothing.

Although various of the breathable barriers described above have proven useful in such absorbent articles as disposable diapers and sanitary napkins, there still is a need for an effective breathable outer cover or baffle which has a clothlike feel and can be manufactured cheaply in large quantities.

SUMMARY OF THE INVENTION

It therefore is an object of the present invention to provide a breathable, multilayered, clothlike barrier.

Another object of the present invention is to provide a breathable, multilayered, clothlike barrier which is especially well suited for use as an outer cover or baffle in such disposable absorbent articles as diapers, sanitary napkins, and incontinent pads.

These and other objects will be apparent to one having ordinary skill in the art from a reading of the specification and claims which follow.

Accordingly, the present invention provides a breathable, multilayered, clothlike barrier which comprises at least three layers:

A. a first layer which is a porous meltblown nonwoven web having a first side and a second side;

B. a second layer joined to said first side of said first layer, which second layer comprises a continuous film of a poly(vinyl alcohol), in which:
   said film is not microporous in that it is substantially free of voids which connect the two surfaces of said film; and
   said film has an average thickness of from about 3 to about 250 microns; and C. a third layer joined to either said second layer or said second side of said first layer, which third layer comprises a porous nonwoven web;

wherein the first layer side of said second layer is intimately comingled with at least some of the fibers at the surface of said first side of said first layer, none of the pores at the surface of said first side of said first layer are so large as to significantly adversely affect the barrier properties of said barrier as a consequence of said comingling, and said barrier has a water vapor transmission rate at 37 degrees C. and about 50 percent relative humidity of from about 100 to about 5,000 g/m²/24 hour and is impermeable to 0.9 percent by weight saline solution at about 21 degrees C. for a period of at least about one hour at a hydrostatic head of at least about 11.4 cm.

In preferred embodiments, the third layer is either a meltblown or a spunbonded web, or a laminate of the two. In other preferred embodiments, the breathable, multilayered, clothlike barrier of the present invention includes up to three additional layers which independently are either a poly(vinyl alcohol) film similar to the second layer or a porous nonwoven web, such as a meltblown or a spunbonded web.

DETAILED DESCRIPTION OF THE INVENTION

As already noted, the breathable, multilayered, clothlike barrier of the present invention is especially well suited for use as an outer cover or baffle in such absorbent articles as disposable diapers, sanitary napkins, and incontinent pads. For this reason, the discussion herein focuses primarily on such use. However, the barrier of the present invention can be employed in any product where water impermeability and water vapor permeability are either desired or necessary characteristics. Consequently, such discussion is not to be construed as in any way limiting either the spirit or scope of the present invention.

As used herein, the term "breathable, multilayered, clothlike barrier" means a multilayered, clothlike composite which is permeable to water vapor but which is impermeable to 0.9 percent by weight saline solution at a temperature of about 21 degrees C. for a period of at least about one hour at a hydrostatic head of at least about 11.4 cm. The composite is permeable to water vapor for the purposes of the present invention if it has a water vapor transmission rate at 37 degrees C. and about 50 percent relative humidity of from about 100 to about 5,000 g/m²/24 hours.

As already stated, the first layer is a porous meltblown nonwoven web. In general, any thermoplastic polymer can be used to prepare the first layer by methods which are well known to those having ordinary skill in the art. See, by way of example, U.S. Pat. Nos. 3,016,599, 3,755,527, 3,704,198, 3,849,241, and 4,100,324, all of which are incorporated herein by reference. Thus, the thermoplastic polymer can be a polyester, polyamide, polyurethane, polyolefin, combinations thereof, and the like. The preferred materials for the preparation of the first layer are polyolefins.

For the purposes of the present disclosure, the term "polyolefin" is meant to include any polymeric material a major constituent of which, i.e., at least 50 percent by weight, is a polyolefin. Thus, the term includes homopolymers, copolymers, and polymer blends.

Copolymers can be random or block copolymers of two or more polyolefins (or two or more different polyolefin monomeric precursors) or of one or more polyolefins and one or more nonpolyolefin polymers. Similarly, polymer blends can utilize two or more polyolefins or one or more polyolefins and one or more nonpolyolefin polymers. As a practical matter, homopolymers and copolymers and polymer blends involving only polyolefins are preferred, with homopolymers being most preferred.

Examples of polyolefins include polyethylene, polystyrene, poly(vinyl chloride), poly(vinyl acetate), poly(vinylidene chloride), poly(acrylic acid), poly(methacrylic acid), poly(methyl methacrylate), poly(ethyl acrylate), polyacrylamide, polyacrylonitrile, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, and the like.

The preferred polyolefins are those prepared from unsaturated hydrocarbon monomers, with polyethylene and polypropylene being most preferred.

The characteristics of the first layer, such as fiber diameter or denier, basis weight, and the like are not critical, provided that such characteristics, in combination with the other layers required by the present invention, particularly in combination with the second layer, achieve the barrier properties specified herein. Those having ordinary skill in the art should appreciate that such characteristics are interrelated with the characteristics of the other layers in general and with those of the second layer in particular. For example, increasing the thickness of the second layer in turn permits the use of a first layer having a lower basis weight or a more loose, less dense construction.

As a practical matter, the basis weight of the first layer typically will be in the range of from about 13.6 to about 34 g per square meter or $g/m^2$. However, lower or higher basis weights can be employed, if desired, depending upon the particular construction and application.

The second layer is a continuous film of a poly(vinyl alcohol), which film is formed in situ from a coating of an aqueous solution of the poly(vinyl alcohol) on the first side of the first layer. Consequently, the first layer side of the second layer is intimately comingled with at least some of the fibers at the surface of the first side of the first layer because the aqueous coating solution to some extent flows into the surface of the first side of the first layer. Thus, the coating solution bridges some fibers while partially or completely enveloping others.

The method of formation of the second layer imposes a limitation on the porosity characteristics of the first side of the first layer. Such limitation is that none of the pores at the surface of the first side of the first layer can be so large as to significantly adversely affect the barrier properties of the barrier of the present invention as a consequence of the comingling phenomenon just described. That is, the ability of the coating solution to bridge pores is not unlimited. Hence, the pores at the surface of the first side of the first layer must be sized so as not to exceed the bridging ability of the coating solution. However, perfection in the formation of the film which is the second layer is not required. Imperfections, such as holes or cracks, can be tolerated as long as the barrier properties of the barrier are not significantly adversely affected. In other words, imperfections are acceptable if they do not diminish the water impermeability of the barrier to a level which is unacceptable for the use intended.

By way of illustration, it is estimated that, in order to obtain generally satisfactory barrier properties, at least about 50 percent of the pores at the surface of the first side of the first layer should have a cross-sectional area of less than about $3.2 \times 10^{-8}$ $m^2$, with none of such pores being so large as to result in the formation of the continuous film in such a manner as to significantly adversely affect the barrier properties of the barrier. Moreover, it is believed that optimum barrier properties should be possible when essentially none of the pores at such surface of the first layer have a cross-sectional area in excess of about $3.2 \times 10^{-8}$ $m^2$. Because of the numerous combinations of first layer and poly(vinyl alcohol) compositions which are possible, however, it is not feasible to do more than offer the foregoing guidelines with respect to the porosity of the first layer, i.e., the porous meltblown nonwoven web.

It perhaps may be noted at this point that the present invention is unique in part because it permits the use of very thin second layers without sacrificing barrier properties. Such very thin second layers apparently are possible because there seems to be a kind of synergistic relationship between the first and second layers, about which more will be said later. Moreover, because the second layer results from a coating of a poly(vinyl alcohol) solution on the first layer, the interface between the two layers necessarily is imprecise. That is, when the coating dries to form a film, the side of the film adjacent to the first layer is intimately comingled with at least some of the fibers of the first side of the first layer. Such comingling, coupled with the adhesive properties of poly(vinyl alcohol), assures the joining of the second layer to the first layer.

Thus, one goal of the present invention is to keep the second layer, as well as all other layers, relatively thin. Consequently, some experimentation may be required to determine the optimum performance of the resulting breathable, multilayered, clothlike barrier for any given application. However, undue experimentation will not be required if the guidelines described herein are followed.

An important aspect of the present invention is the fact that the poly(vinyl alcohol) film which comprises the second and some other layers is not a microporous film as that term has been used in the art. That is, the poly(vinyl alcohol) film utilized in the present invention does not have voids or micropores which connect the two surfaces of the film. In a microporous film, the interconnecting voids provide a pathway for the transport of water molecules from one surface to another, the driving force being the differences in relative humidities at the two surfaces. The poly(vinyl alcohol) film employed in the present invention, however, utilize a different mechanism, namely: water molecules are soluble in the film and capable of being transported by means of such solubility from one surface of the film to the other.

As already noted, the average thickness of the second layer should be in the range of from about 3 to about 250 microns. Preferably, the average thickness of the second layer will be in the range of from about 3 to about 85 microns, more preferably from about 3.4 to about 15 microns, and most preferably from about 5 to about 12 microns.

It should be noted that average film thicknesses are involved. Because of the inherent relative roughness of the surfaces of many meltblown webs, film thicknesses must vary over the area of the second layer. This necessitates dealing with average film thicknesses. Moreover, the average film thickness is an adequate measure of the amount of the continuous film which constitutes the second layer. Stated differently, some variability or imprecision in film thickness is acceptable since the barrier properties of the film do not appear to be extremely sensitive to film thickness.

A related problem is the difficulty of accurately measuring film thickness. For the purposes of the present invention, it is sufficient if film thicknesses are only estimated. A reasonable estimate of the thickness of a film can be made from the amount of add-on of the PVOH resin or PVOH composition if the density of the resin or composition is known. With the poly(vinyl alcohol) resins employed in the example, it was found that each $g/m^2$ of add-on was approximately equivalent to 0.85 micron of film thickness.

If a fourth layer is present which is a continuous film of a poly(vinyl alcohol), and the fourth layer is joined to the second layer, then both the second and fourth layer thicknesses can be reduced. Under these conditions, the preferred range for the thickness of each layer is from about 1.5 to about 85 microns, with a range of from about 1.5 to about 12 microns being more preferred. The most preferred thickness range for each of the two adjacent layers is from about 1.5 to about 10 microns.

As is well known in the art, poly(vinyl alcohol), from which the second layer is prepared, is a synthetic water-soluble polymeric material. There are, however, numerous grades of poly(vinyl alcohol), many of which have different solubility characteristics in water. For example, some grades are soluble in water at ambient temperature, while others are soluble in water only at elevated temperatures. At the present time, though, there are no known limitations with respect to the grade or nature of the poly(vinyl alcohol) employed in the preparation of the second layer.

Poly(vinyl alcohol), for convenience often referred to hereinafter as PVOH, is produced by the hydrolysis of poly(vinyl acetate). PVOH is available commercially in several grades which differ in degree of polymerization and degree of hydrolysis. In general, the degree of polymerization will vary from about 500 to about 2,500; the corresponding molecular weights are from about 22,000 to about 110,000. The degree of hydrolysis usually will vary from about 85 percent to essentially 100 percent (e.g., 99.7 percent minimum hydrolysis). In addition, some modified PVOH materials also are available, such as so-called tackified grades which are borated PVOH resins (see U.S. Pat. No. 3,135,648).

Typical of the commercially available PVOH resins are the VINOL resins available from Air Products and Chemicals, Inc., Polymer Chemicals, Allentown, Pennsylvania.

Preferably, the PVOH resin will have a relatively high degree of hydrolysis, typically essentially completely hydrolyzed, since such a resin does not require the use of a crosslinking agent.

Although resins having a lower degree of hydrolysis can be employed with satisfactory results, such resins may require the presence of a crosslinking agent in the aqueous solution of PVOH with which the first layer is coated, depending upon the use intended for the barrier, since such resins often are quite soluble in water at ambient temperature. However, inclusion of a crosslinking agent is not required, even for such resins.

One of the remarkable aspects of the present invention is the fact that such resins can be used to prepare satisfactory breathable barriers. There are a number of porous sheets, meltblown webs in particular, which exhibit barrier properties with respect to liquid water. Such barrier properties, however, generally are insufficient to permit such porous sheets to serve by themselves as breathable barriers having the properties associated with the barriers of the present invention. Nevertheless, such sheets, when joined with a continuous film of a water-soluble polymer as provided herein, yield barriers having properties which exceed the sum of the properties of the individual components making up the barrier. That is, there is a kind of synergy which results from the combination of a porous sheet having significant barrier properties with a continuous film of a water soluble polymeric material as provided by the present invention. For some applications, the porous sheet permits the use of polymeric materials which are quite soluble in water at ambient temperature. As a practical matter, however, it is preferred that such continuous film is substantially insoluble in water having a temperature less than about 50 degrees C.

Suitable crosslinking agents are those known in the art, such as glyoxal; formaldehyde; urea-formaldehydes; melamine-formaldehydes; metal compounds, such as cupric ammonium complexes, chromium complexes, organic titanates, and dichromates; and the like. When required, a crosslinking agent usually is employed in an amount in the range of from about 1 to about 5 percent by weight, based on the dry weight of PVOH, although higher or lower amounts can be employed, if desired.

In addition to the use of chemical crosslinking agents as discussed above, the formed PVOH film can be crosslinked by radiation, such as electron beam radiation, ultraviolet radiation, and the like. The formed PVOH film also can be crosslinked thermally by heating the film to a temperature in excess of 100 degrees C. The preferred temperature range is from about 120 to about 180 degrees C. In the preferred temperature range, the crosslinking time typically is about one hour. Thermal crosslinking is preferred over the use of a chemical crosslinking agent.

Because flexibility of the breathable, multilayered, clothlike barrier often is a required characteristic, it may be either necessary or desirable to include a plasticizer in the PVOH film. Suitable plasticizers in general are any of the known plasticizers for PVOH, such as glycerol, the poly(oxyethylene) diols, pentaerythritol, 1,2,6-hexanetriol, sorbitol, formamide, urea, and the like. Glycerol has been found to be a particularly useful plasticizer and is preferred. Thus, a plasticizer can be present in an amount of from 0 to about 50 percent by weight, based on the dry weight of PVOH employed, although somewhat higher amounts perhaps can be used, depending upon the grade of poly(vinyl alcohol) and the plasticizer. When employed, the plasticizer preferably will be present in an amount of from about 15 to about 25 percent by weight.

Some care must be exercised in the use of plasticizers, however. While plasticizers can increase film flexibility and enhance film formation, they also can adversely affect the liquid water barrier characteristics of the breathable barrier, especially when used at unusually high levels. Thus, the plasticizer level in general should be kept to the minimum level which is consistent both with film formation and flexibility requirements and the desired properties of the breathable barrier.

As indicated hereinbefore, the PVOH is applied to a first side of the first layer as an aqueous solution. Application usually is made at ambient temperature and pressure, although such conditions are not mandatory. Indeed, any combination of temperature and pressure can be employed, although for reasons of economics and convenience, ambient temperature and pressure are preferred.

The concentration of PVOH in the solution is not known to be critical and usually is a matter of convenience. In practice, concentrations of from about 4 to about 12 percent by weight are typical. The preferred concentration range is from about 5 to about 8 percent by weight.

The method of application is not known to be critical and largely is a matter of convenience. Thus, the PVOH solution can be applied by spraying, dipping, brushing, doctor blade, roller, Meyer rod, and the like. The use of a Meyer rod is preferred. In addition, a single coat or multiple coats can be applied. Moreover, if multiple coats are applied, the application solution does not have to be the same for each application. The several solutions can utilize different concentrations of PVOH, the presence or absence of such compounds as crosslinking agent and plasticizer, the presence or absence of other additives, or combinations of any of the foregoing variations.

The amount of PVOH present in said second layer typically will be in the range of from about 3 to about 15 $g/m^2$. Of course, lower or higher amounts can be employed, if desired, as long as such amounts are consistent with the thickness ranges specified herein for the second layer and other layers which also are continuous films of a poly(vinyl alcohol). When two adjacent poly(vinyl alcohol) layers are present, the amount of PVOH present in each layer usually will be in the range of from about 2 to about 6 $g/m^2$.

After the aqueous solution of water-soluble polymeric material has been applied to the first layer, the resulting combination is dried by removing water, preferably at an elevated temperature. Upon drying, a continuous film of poly(vinyl alcohol) is formed which is contiguous with and adherent to said first side of said first layer. Thus, the resulting second layer overlays and is joined to the first layer. If a subsequent layer is to be applied overlaying and joined to the resulting PVOH film or second layer, such application can be done before drying has been completed and is preferred when the subsequent layer is a porous nonwoven web since the PVOH has adhesive properties.

Finally, additives other than crosslinking agents and plasticizers can be incorporated into the PVOH film, if desired. Such additives include binders, extenders, fillers, pigments, dyes, defoamers, preservatives, fungicides, wetting agents, deodorants, fluorescent agents, latexes, fluorocarbons, water-repellent extenders, waxes, and the like. Incorporation is accomplished by simply dissolving or dispersing such additives in the aqueous coating solution.

The third layer in general can be any porous nonwoven web. Preferably, the third layer will be either a spunbonded or meltblown web, or a laminate of the two (a laminate of the two can be considered to be a third layer and a fourth layer which are joined together, and is treated as such herein). As with the first layer, the thermoplastic polymer used to prepare the third layer and the characteristics of the prepared web are not known to be critical. The preferred thermoplastic polymers are polyolefins, with polypropylene and polyethylene being most preferred. Finally, the third layer can be joined to either the second layer or to the second side of the first layer.

When the third layer is a spunbonded web, the basis weight of the third layer typically will be in the range of from about 17 to about 34 $g/m^2$. For an example of a spunbonded process, see U.S. Pat. No. 3,692,618, which is incorporated herein by reference.

Additional layers can be added to the breathable, multilayered, clothlike barrier of the present invention as desired. If present, such additional layers will be selected from the group consisting of a PVOH film and a porous nonwoven web. The PVOH film will have characteristics similar to the second layer and the webs will be similar to the first and third layers described hereinbefore.

Although the various layers which comprise the breathable, multilayered, clothlike barriers of the present invention must be joined to each other, the method of joining is not critical. Indeed, any of the known methods of joining two sheets together can be employed. Such methods include thermal bonding, chemical or adhesive bonding, solvent bonding, ultrasonic bonding, laser bonding, needle punching, hydraulic entanglement, and the like.

As noted already, the breathable, multilayered, clothlike barrier of the present invention should have a water vapor transmission rate (WVTR) at 37 degrees C. and about 50 percent relative humidity of from about 100 to about 5,000 $g/m^2/24$ hours the WVTR preferably will be in the range of from about 500 to about 4,000 $g/m^2/24$ hours, and most preferably from about 1,000 to about 3,000 $g/m^2/24$ hours.

Figure 1:
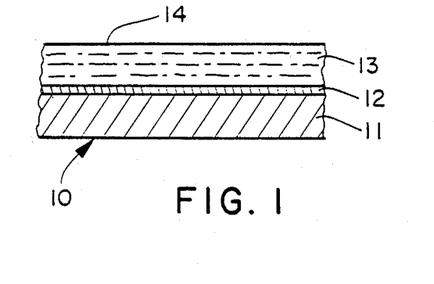
FIGS. 1 and 2 are diagrammatic representations of cross-sectional views of the most general and most simple forms of breathable, multilayered, clothlike barriers coming within the scope of the present invention.
Figure 2:
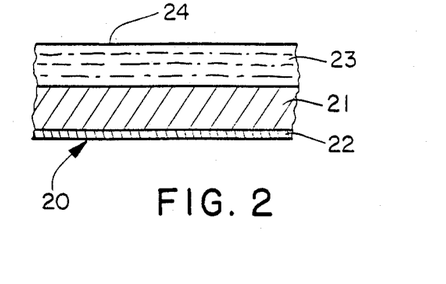

The most general and most simple forms of breathable, multilayered, clothlike barriers coming within the scope of the present invention are illustrated diagrammatically in cross-section by FIGS. 1 and 2. In FIG. 1, barrier 10 comprises first layer 11 which is a meltblown web to which is joined second layer 12 which is a continuous film of a poly(vinyl alcohol). Third layer 13, which is a porous nonwoven web, in turn is joined to second layer 12. In most applications, the outermost or OM surfaces (which in a disposable diaper typically is referred to as the motherside) will be surfaces 14 and 24, respectively, in FIGS. 1 and 2.

To obtain the barrier of FIG. 1, a meltblown web is coated with an aqueous solution of a poly(vinyl alcohol). Before the coating is dried, a porous nonwoven web is applied to the coated side of the meltblown web. Upon drying the resulting composite, the barrier of FIG. 1 is obtained.

The barrier of FIG. 2 is most easily obtained by laminating a porous nonwoven web to a first side of a meltblown web by any known means. The second side of the meltblown web then is coated with an aqueous poly(vinyl alcohol) solution. The resulting composite then is dried.

FIGS. 3–13, inclusive, represent certain preferred embodiments, including the embodiment as prepared in the Example.

Figure 3:
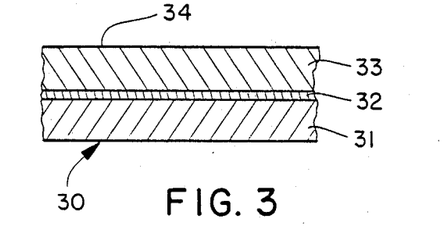
FIGS. 3–13 inclusive, are diagrammatic representations of cross-sectional views of various preferred embodiments of the present invention. The embodiment represented by FIG. 10 is the barrier prepared in the Example.

Turning now to FIG. 3, barrier 30 comprises first layer 31 which is a meltblown web, second layer 32 which is a continuous film of a poly(vinyl alcohol), and third layer 33 which is a spunbonded web. The OM surface usually will be surface 34. The barrier 30 represented by FIG. 3 is the barrier 10 of FIG. 1 when the third layer is a spunbonded web. The barrier is readily prepared as described for the barrier of FIG. 1, except that the porous nonwoven web in this case is a spunbonded web. The meltblown web typically will have a basis weight of from about 13.6 to about 34 $g/m^2$. The PVOH usually will be plasticized with, for example, from about 15 to about 25 percent by weight, based on the dry weight of the PVOH resin, of glycerol. The concentration of PVOH in the coating solution typically will be from about 4 to about 10 percent by weight. The dry weight add-on of PVOH to the meltblown web ordinarily is from about 3 to about 15 $g/m^2$. Finally, the spunbonded web often will have a basis weight of from about 17 to about 34 $g/m^2$.

Figure 4:
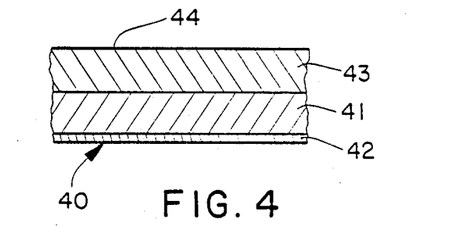

FIG. 4 represents a specific example of the barrier 20 illustrated by FIG. 2. In FIG. 4, barrier 40 is composed of layers 41, 42, and 43 which are equivalent to layers 21, 22, and 23, respectively, of FIG. 2, except that layer 43 is a spunbonded web. The OM surface usually will be surface 44. Barrier 40 is readily prepared by the method described for the preparation of barrier 20. The basis weights of meltblown layer 41 and spunbonded layer 43 usually are in the range of from about 17 to about 34 $g/m^2$. The PVOH layer 42 generally is similar to layer 32 of barrier 30 in FIG. 3.

Figure 5:
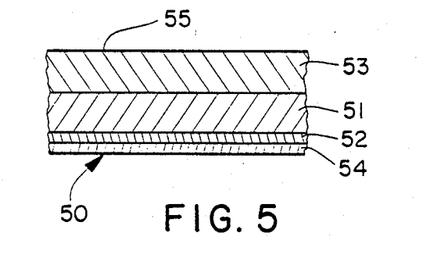

The barrier 50 of FIG. 5 is the barrier of FIG. 4 to which a fourth layer 54 has been added. This fourth layer 54 is overlaying and joined to layer 52 and is similar to layer 52. The OM surface typically is surface 55. Because the barrier 50 includes two PVOH film layers, the add-on for each layer typically can be reduced to from about 2 to about 6 $g/m^2$. In preparing the barrier 50, the composite is dried after the application of the PVOH solution from which layer 52 is formed. A second coating of the same or a different PVOH solution then is applied and the resulting composite dried.

Figure 6:
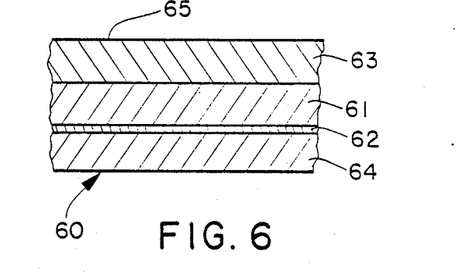

If layer 54 of the barrier of FIG. 5 is replaced with a meltblown web, the barrier of FIG. 6 results. Consequently, the method of making the barrier of FIG. 5 applies to barrier 60; all that is necessary is to replace layer 54 with a meltblown web before drying the PVOH coating which is the precursor of layer 52. In FIG. 6, barrier 60 comprises first layer 61 which is a meltblown web, second layer 62 which is a continuous film of a poly(vinyl alcohol), and third and fourth layers 63 and 64, respectively, each of which is a spunbonded web. The OM surface typically is surface 65. Each layer ordinarily will have the same characteristics as described for similar layers of the barriers of the Figures discussed above. In fact, the same is generally true for each layer of the barriers represented by FIGS. 3-16, inclusive.

Figure 7:
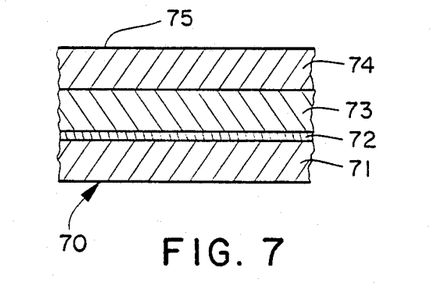

Barrier 70 of FIG. 7 comprises first layer 71 which is a meltblown web, second layer 72 which is a continuous film of a poly(vinyl alcohol), third layer 73 which is a spunbonded web, and fourth layer 74 which is a meltblown web. Thus, the barrier has two meltblown layers and one spunbonded layer. The OM surface ordinarily will be surface 75. The barrier can be prepared by laminating a spunbonded web to a meltblown web as already described. A separate meltblown web is coated with a PVOH solution and, before the coating is dried, is combined with the spunbonded-meltblown laminate with the spunbonded side overlaying and contiguous with the PVOH coating. Upon drying the resulting composite, the barrier 70 is obtained.

Figure 8:
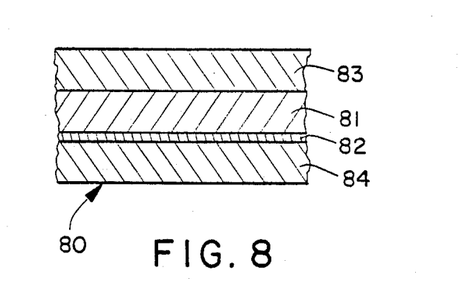

The barrier of FIG. 8 is similar to that of FIG. 7 except that barrier 80 has two spunbonded layers and one meltblown layer; layers 83 and 84 are spunbonded webs and layer 81 is a meltblown web. Construction of the barrier involves preparing a spunbonded-meltblown laminate as described with respect to FIG. 7, coating the laminate on the meltblown side with a PVOH solution, and overlaying the coated side of the laminate with a spunbonded web. Drying the resulting composite gives the barrier 80.

Figure 9:
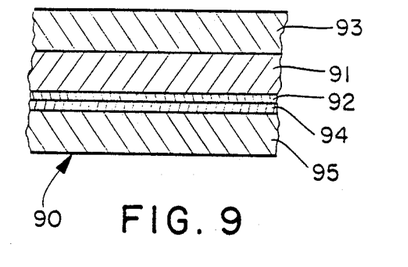

The addition of a spunbonded fifth layer to the barrier of FIG. 5 results in Barrier 90 of FIG. 9. Thus, barrier 90 comprises first layer 91 which is a meltblown web, second layer 92 which is a continuous film of a poly(vinyl alcohol), third layer 93 which is a spunbonded web, fourth layer 94 which is a continuous film of a poly(vinyl alcohol), and fifth layer 95 which is the added spunbonded web already mentioned. Barrier 90 can be made in the same manner as the barrier of FIG. 5, with the added step of placing layer 95 over the PVOH coating which is the precursor for layer 94. Barrier 90 then is obtained upon drying the composite after layer 95 is in place.

Figure 10:
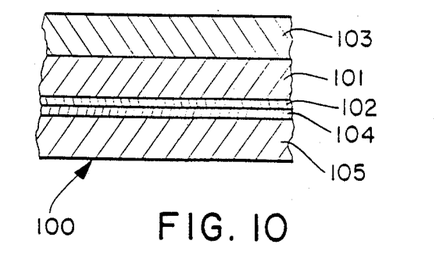

The barrier of FIG. 10, which is the barrier described in the Example, is similar to that of FIG. 9, except that the fifth layer in barrier 100 is a meltblown web, rather than the spunbonded web of barrier 90. As already noted, the preparation of barrier 100 is described in the Example.

Figure 11:
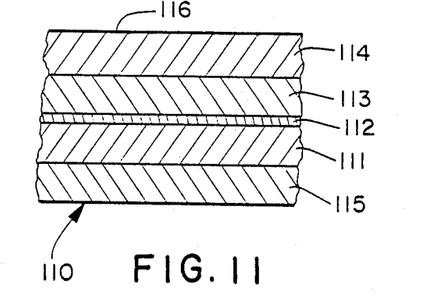

FIG. 11 illustrates a barrier 110 which in effect is the barrier of FIG. 7 to which a fifth, spunbonded layer has been added. Accordingly, barrier 110 comprises first layer 111 which is a meltblown web, second layer 112 which is a continuous film of a poly(vinyl alcohol), third layer 113 which is a spunbonded web, fourth layer 114 which is a meltblown web, and fifth layer 115 which is a spunbonded web. The barrier 110 is readily prepared by the procedure described for the barrier of FIG. 7 by using a spunbonded-meltblown laminate in place of the meltblown web used to prepare barrier 70; the PVOH coating, of course, is applied to the meltblown side of the laminate.

Figure 12:
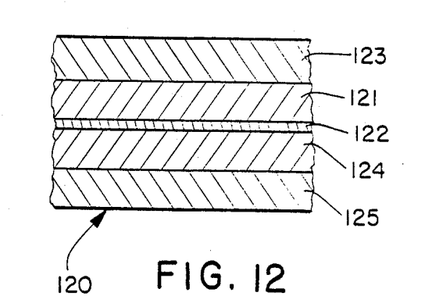

Barrier 120 of FIG. 12 is the barrier of FIG. 6 to which a fifth, spunbonded layer has been added. Consequently, barrier 120 comprises first layer 121 which is a meltblown web, second layer 122 which is a continuous film of poly(vinyl alcohol), third layer 123 which is a spunbonded web, fourth layer 124 which is a meltblown web, and fifth layer 125 which is a spunbonded web. Barrier 120 is prepared as described for barrier 60 simply by replacing the meltblown web which becomes layer 64 with a spunbonded-meltblown laminate with the meltblown side overlaying and contiguous with the PVOH coating.

Figure 13:
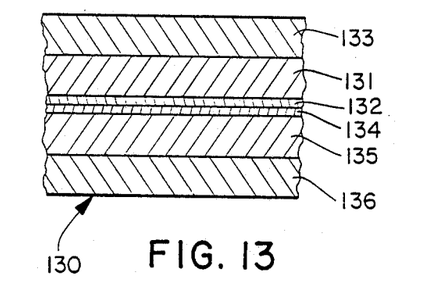

FIG. 13 illustrates barrier 130 which is the barrier of FIG. 12 to which a second continuous film of a poly(vinyl alcohol) has been added. Thus, barrier 130 comprises first layer 131 which is a meltblown web, second layer 132 which is a continuous film of a poly(vinyl alcohol), third layer 133 which is a spunbonded web, fourth layer 134 which is a continuous film of a poly(vinyl alcohol), fifth layer 135 which is a meltblown web, and sixth layer 136 which is a spunbonded web. The barrier of FIG. 13 is prepared much as described for that of FIG. 12. The only change will be the addition of a second PVOH coating over the first one after the first one has been dried. Of course, the second PVOH coating is not dried until after the spunbonded-meltblown laminate which will become layers 135 and 136 has been placed over the second PVOH coating.

Figure 14:
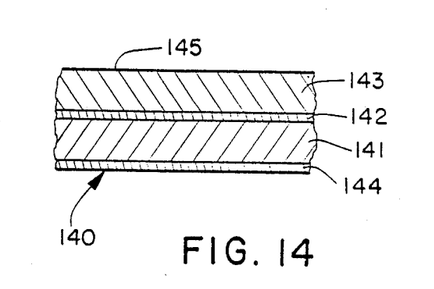
FIGS. 14–16, inclusive, are diagrammatic representations of cross-sectional views of various other embodiments of the present invention.
Figure 15A:
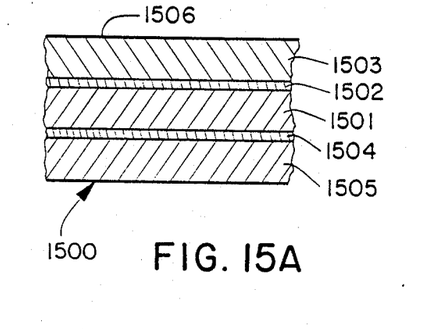
Figure 15B:
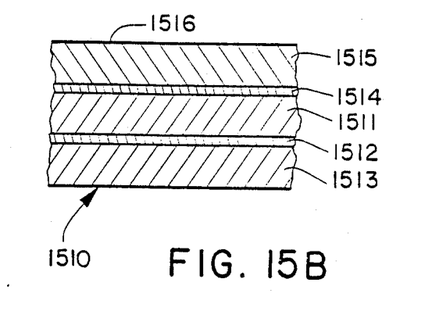
Figure 16:
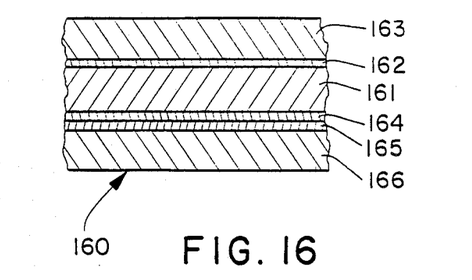

FIGS. 14-16, inclusive, represent other embodiments of the present invention, by way of illustration only, in which the barriers include at least two layers of a continuous film of a poly(vinyl alcohol) which are not overlaying and contiguous with each other.

FIG. 14 represents the barrier of FIG. 3 to which a fourth layer which is a continuous film of a poly(vinyl alcohol) has been added. The barrier 140 can be prepared by coating the meltblown side of barrier 30 with a PVOH solution and drying the resulting composite. In most instances, the OM surface will be surface 145.

FIGS. 15A and 15B represent a barrier which can be considered as being the barrier of FIG. 6 with an added layer between first layer 61 and third layer 63, which added layer is a continuous film of a poly(vinyl alcohol); although the barrier is the same in both figures, the barriers and layers have been numbered differently for convenience in referring to methods of preparing the barrier. The barrier of these figures can be prepared by at least two different, although related, procedures. Turning now to FIG. 15A, barrier 1500 is prepared by coating a meltblown web with an aqueous solution of a poly(vinyl alcohol). Before the PVOH coating is dried, a spunbonded web is applied over the PVOH coating. If desired, the resulting composite can be dried at this stage. A second PVOH coating then is applied to the meltblown side of the resulting intermediate composite, followed by overlaying a second meltblown web on the second PVOH coating. Drying the composite thus obtained yields barrier 1500. Alternatively, the second PVOH coating can be applied to the second meltblown web and the resulting two-layer structure applied to the intermediate composite, PVOH-coated side to meltblown side, respectively. Thus, barrier 1500 comprises first layer 1501 which is a meltblown web, second layer 1502 which is a continuous film of a poly(vinyl alcohol), third layer 1503 which is a spunbonded web, fourth layer 1504 which is a continuous film of a poly(vinyl alcohol), and fifth layer 1505 which is a meltblown web. The OM surface normally will be surface 1506.

The preparation of barrier 1510 of FIG. 15B is similar, in that such preparation also begins with a meltblown web which is coated with an aqueous solution of a poly(vinyl alcohol). The PVOH coating is overlayed with a meltblown web and either meltblown side of the resulting intermediate composite is coated with an aqueous solution of a poly(vinyl alcohol) to which a spunbonded web is applied. Drying the structure gives the barrier of FIG. 15B. If desired, the second PVOH coating can be applied to the spunbonded web which then is placed against the intermediate composite. Hence, barrier 1510 comprises first layer 1511 which is a meltblown web, second layer 1512 which is continuous film of a poly(vinyl alcohol), third layer 1513 which is a meltblown web, fourth layer 1514 which is a continuous film of a poly(vinyl alcohol), and fifth layer 1515 which is a spunbonded web. The most likely OM surface is surface 1516.

Finally, barrier 160 of FIG. 16 comprises first layer 161 which is a meltblown web, second layer 162 which is a continuous film of a poly(vinyl alcohol), third layer 163 which is a spunbonded web, fourth layer 164 which is a continuous film of a poly(vinyl alcohol), fifth layer 165 which also is a continuous layer of a poly(vinyl alcohol), and sixth layer 166 which is a spunbonded web. The barrier 160 can be prepared, by way of example, by coating a meltblown web with an aqueous solution of a poly(vinyl alcohol) and placing a spunbonded web against the PVOH coating to get an intermediate composite. The meltblown side of the intermediate composite is coated with an aqueous solution of a poly(vinyl alcohol) and the resulting composite is dried. A third PVOH coating is applied over the last-applied PVOH coating. A spunbonded web then is placed against the third PVOH coating and the resulting structure is dried to give barrier 160. If desired, the third PVOH coating can be applied to the single spunbonded web and the resulting coated web placed against the multilayered intermediate composite, PVOH-coated side to PVOH-coated side.

The present invention is further described by the example which follows, illustrating one preferred embodiment of the present invention. Such example is not to be construed as in any way limiting either the spirit or scope of the present invention.

In the example, the water vapor transmission rate was determined in accordance with ASTM Method E 96-80, Standard Test Methods for Water Vapor Transmission of Materials, Procedure 12. The apparatus employed was a Vapometer (Catalog No. 68-1, Thwing-Albert Instrument Company, Philadelphia, Pa.). The apparatus consisted of a two-inch (about 5.1-cm) deep aluminum cup having a flanged top with a neoprene rubber gasket. The inner diameter of the flange was 2.5 inches (about 6.4 cm). About 100 ml of water was added to the cup and a sample of the barrier to be tested was sealed mechanically over the open end of the cup and weighed. The sample-cup assembly was placed in an oven at 37 degrees C. and about 50 percent relative humidity. Periodic weighings of the sample-cup assembly permitted calculation of the water vapor transmission rate (WVTR).

The effectiveness of the breathable, multilayered, clothlike barrier as a barrier to liquid water was measured by INDA Standard Test 80.7-70 (82), INDA Standard Test for Saline Repellency of Nonwovens, often referred to as the Mason Jar Test. The test liquid was 0.9 percent by weight saline solution.

EXAMPLE

A four percent by weight aqueous solution of poly(vinyl alcohol) was prepared by dispersing the resin in an aqueous solution of 1 percent by weight glycerol in water at ambient temperature and heating the mixture at about 205 degrees with moderate agitation until the resin dissolved. The poly(vinyl alcohol) employed was VINOL 165 (Air Products and Chemicals, Inc., Polymer Chemicals, Allentown, Pennsylvania). According to information supplied by the manufacturer, the resin was in excess of 99.3 percent hydrolyzed and a 4 percent by weight aqueous solution of the resin at 20 degrees had a viscosity of 55–65 cps. The resulting solution then was allowed to cool to ambient temperature.

A spunbonded polypropylene web having a basis weight of about 23.8 g/m$^2$ was bonded to a meltblown polypropylene web having a basis weight of about 17 g/m$^2$. Bonding was accomplished by the patterned application of heat and pressure, in which the pattern was diamond shaped and represented approximately 15 percent of the total surface area and the bonding temperature was 270–280 degrees F. (132–137 degrees C.). The meltblown side of the resulting laminate was coated with the poly(vinyl alcohol) solution with a roll coater and Meyer rod and dried at about 300 degrees F. (about 149 degrees C.). The average add-on of resin was about 2 g/m$^2$ on a dry-weight basis. A second coat of poly(vinyl alcohol) was applied over the first coat at an average add-on of 3 g/m$^2$ on a dry-weight basis. A meltblown polypropylene web having a basis weight of 17 g/m$^2$ was immediately layed over the second coat and the resulting multilayered composite was dried again at about 300 degrees F. (about 149 degrees C.).

The breathable, multilayer, clothlike barrier thus obtained passed the Mason Jar Test and gave a WVTR of 2500 g/m$^2$/24 hours.

Figure 17:
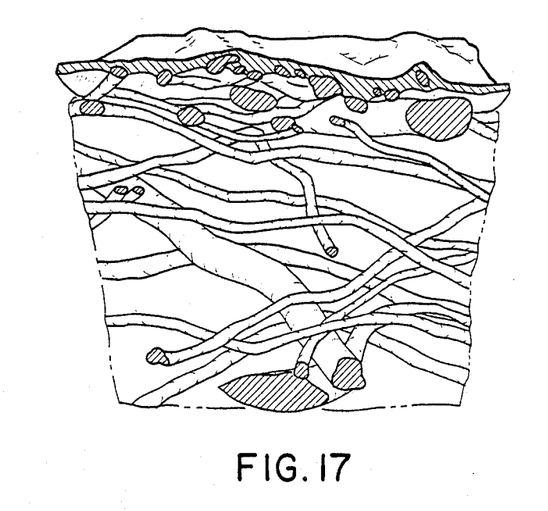
FIGS. 17 and 18 are representations of cross-sectional view scanning electron micrographs of a polypropylene meltblown nonwoven web coated once with a poly(vinyl alcohol) solution as described in the Example.
Figure 18:
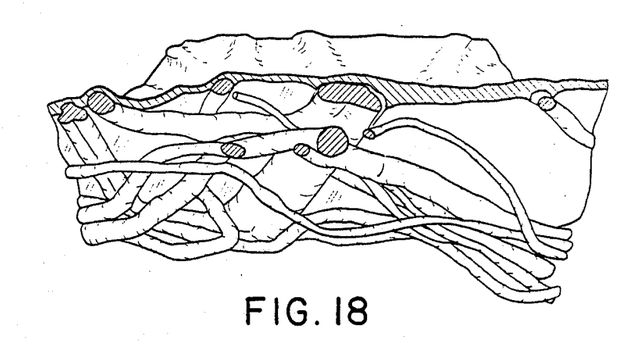

A polypropylene meltblown web coated once as described in the Example was examined in cross-section by scanning electron microscopy. FIGS. 17 and 18 are representations of the micrographs obtained at a magnification of 1000X. The very thin nature of the resulting film and the comingling phenomenon described earlier are readily apparent.

Having thus described the present invention, numerous changes and modifications thereof will be apparent to those having ordinary skill in the art without departing from either the spirit or the scope of the invention. For example, numerous barriers other than those illustrated by FIGS. 3–16, inclusive, can be constructed. Moreover, the characteristics given as representative of the various layers of the barriers of the figures can be altered as desired.

What is claimed is:

1. A breathable, multilayered, clothlike barrier which comprises at least three layers:
   A. a first layer which is a porous meltblown nonwoven web having a first side and a second side;
   B. a second layer joined to said first side of said first layer, which second layer comprises a continuous film of a poly(vinyl alcohol), in which:
      said film is not microporous in that it is substantially free of voids which connect the two surfaces of said film; and
      said film has an average thickness of from about 3 to about 250 microns; and
   C. a third layer joined to either said second layer or said second side of said first layer, which third layer comprises a porous nonwoven web;
   wherein the first layer side of said second layer is intimately comingled with at least some of the fibers at the surface of said first side of said first layer, none of the pores at the surface of said first side of said first layer are so large as to significantly adversely affect the barrier properties of said barrier as a consequence of said comingling, and said barrier has a water vapor transmission rate at 37 degrees C. and about 50 percent relative humidity of from about 100 to about 5,000 g/m$^2$/24 hour and is impermeable to 0.9 percent by weight saline solution at about 21 degrees C. for a period of at least about one hour at a hydrostatic head of at least about 11.4 cm.

2. The barrier of claim 1, in which said film is substantially insoluble in water having a temperature less than about 50 degrees C.

3. The barrier of claim 1, in which at least about 50 percent of the pores at the surface of said first side of said first layer each have a cross-sectional area of less than about 3.2×10$^{-8}$ m$^2$.

4. The barrier of claim 1, in which essentially none of the pores at the surface of said first side of said first layer have a cross-sectional area in excess of about 3.2×10$^{-8}$ m$^2$.

5. The barrier of claim 4, in which said first layer is comprised of polyolefin fibers.

6. The barrier of claim 5, in which said polyolefin is polypropylene.

7. The barrier of claim 1, in which said third layer is a spunbonded web.

8. The barrier of claim 7, in which said spunbonded web is comprised of polyolefin fibers.

9. The barrier of claim 8, in which said polyolefin fibers are polypropylene.

10. The barrier of claim 7, in which said third layer is joined to said second layer.

11. The barrier of claim 7, in which said third layer is joined to said second side of said first layer.

12. The barrier of claim 1, in which said third layer is a meltblown web.

13. The barrier of claim 12, in which said meltblown web is comprised of polyolefin fibers.

14. The barrier of claim 13, in which said polyolefin fibers are polypropylene.

15. The barrier of claim 12, in which said third layer is joined to said second layer.

16. The barrier of claim 12, in which said third layer is joined to said second side of said first layer.

17. The barrier of claim 1, in which said barrier includes a fourth layer which comprises a continuous film of a poly(vinyl alcohol), in which:
   said film is not microporous in that it is substantially free of voids which connect the two surfaces of said film; and
   said film has an average thickness of from about 3 to about 250 microns.

18. The barrier of claim 17, in which said film is substantially insoluble in water having a temperature less than about 50 degrees C.

19. The barrier of claim 7, in which said barrier includes a fourth layer which comprises a continuous film of a poly(vinyl alcohol), in which:
   said film is not microporous in that it is substantially free of voids which connect the two surfaces of said film; and
   said film has an average thickness of from about 3 to about 250 microns.

20. The barrier of claim 19, in which said film is substantially insoluble in water having a temperature less than about 50 degrees C.

21. The barrier of claim 11, in which said barrier includes a fourth layer joined to said second layer, said fourth layer comprising a continuous film of poly(vinyl alcohol), in which:
   said film is not microporous in that it is substantially free of voids which connect the two surfaces of said film; and
   said film has an average thickness of from about 3 to about 250 microns.

22. The barrier of claim 21, in which said film is substantially insoluble in water having a temperature less than about 50 degrees C.

23. The barrier of claim 12, in which said barrier includes a fourth layer which comprises a continuous film of a poly(vinyl alcohol), in which:
   said film is not microporous in that it is substantially free of voids which connect the two surfaces of said film; and
   said film has an average thickness of from about 3 to about 250 microns.

24. The barrier of claim 23, in which said film is substantially insoluble in water having a temperature less than about 50 degrees C.

25. The barrier of claim 16, in which said barrier includes a fourth layer joined to said second layer, said fourth layer comprising a continuous film of a poly(vinyl alcohol), in which:

said film is not microporous in that it is substantially free of voids which connect the two surfaces of said film; and said film has an average thickness of from about 3 to about 250 microns.

26. The barrier of claim 25, in which said film is substantially insoluble in water having a temperature less than about 50 degrees C.

27. The barrier of claim 1, in which said barrier includes a fourth layer which is a porous nonwoven web.

28. The barrier of claim 27, in which said fourth layer is a meltblown web.

29. The barrier of claim 27, in which said fourth layer is a spunbonded web.

30. The barrier of claim 7, in which said barrier includes a fourth layer which is a porous nonwoven web.

31. The barrier of claim 29, in which said fourth layer is a meltblown web.

32. The barrier of claim 30, in which said fourth layer is a spunbonded web.

33. The barrier of claim 11, in which said barrier includes a fourth layer which is a porous nonwoven web.

34. The barrier of claim 33, in which said fourth layer is a meltblown web.

35. The barrier of claim 33, in which said fourth layer is a spunbonded web.

36. The barrier of claim 12, in which said barrier includes a fourth layer which is a porous nonwoven web.

37. The barrier of claim 36, in which said fourth layer is a meltblown web.

38. The barrier of claim 36, in which said fourth layer is a spunbonded web.

39. The barrier of claim 16, in which said barrier includes a fourth layer which is a porous nonwoven web.

40. The barrier of claim 39, in which said fourth layer is a meltblown web.

41. The barrier of claim 39, in which said fourth layer is a spunbonded web.

42. The barrier of claim 17, in which said barrier includes a fifth layer which is a porous nonwoven web.

43. The barrier of claim 42, in which said fifth layer is a meltblown web.

44. The barrier of claim 42, in which said fifth layer is a spunbonded web.

45. The barrier of claim 24, in which said barrier includes a fifth layer which is a porous nonwoven web.

46. The barrier of claim 45, in which said fifth layer is a meltblown web.

47. The barrier of claim 45, in which said fifth layer is a spunbonded web.

48. The barrier of claim 17, in which said barrier includes a fifth layer which comprises a continuous film of a poly(vinyl alcohol), in which:

said film is not microporous in that it is substantially free of voids which connect the two surfaces of said film; and said film has an average thickness of from about 3 to about 250 microns.

49. The barrier of claim 48, in which said film is substantially insoluble in water having a temperature less than about 50 degrees C.

50. The barrier of claim 23, in which said barrier includes a fifth layer which comprises a continuous film of a poly(vinyl alcohol), in which:

said film is not microporous in that it is substantially free of voids which connect the two surfaces of said film; and said film has an average thickness of from about 3 to about 250 microns.

51. The barrier of claim 50, in which said film is substantially insoluble in water having a temperature less than about 50 degrees C.

52. The barrier of claim 42, in which said barrier includes a sixth layer which is a porous nonwoven web.

53. The barrier of claim 52, in which said sixth layer is a meltblown web.

54. The barrier of claim 52, in which said sixth layer is a spunbonded web.

55. The barrier of claim 45, in which said barrier includes a sixth layer which is a porous nonwoven web.

56. The barrier of claim 55, in which said sixth layer is a meltblown web.

57. The barrier of claim 55, in which said sixth layer is a spunbonded web.

58. The barrier of claim 48, in which said barrier includes a sixth layer which is a porous nonwoven web.

59. The barrier of claim 58, in which said sixth layer is a meltblown web.

60. The barrier of claim 58, in which said sixth layer is a spunbonded web.

61. The barrier of claim 49, in which said barrier includes a sixth layer which is a porous nonwoven web.

62. The barrier of claim 61, in which said sixth layer is a meltblown web.

63. The barrier of claim 61, in which said sixth layer is a spunbonded web.

64. The barrier of claim 42, in which said barrier includes a sixth layer which comprises a continuous film of a poly(vinyl alcohol), in which:

said film is not microporous in that it is substantially free of voids which connect the two surfaces of said film; and said film has an average thickness of from about 3 to about 250 microns.

65. The barrier of claim 64, in which said film is substantially insoluble in water having a temperature less than about 50 degrees C.

66. The barrier of claim 45, in which said barrier includes a sixth layer which comprises a continuous film of a poly(vinyl alcohol), in which:

said film is not microporous in that it is substantially free of voids which connect the two surfaces of said film; and said film has an average thickness of from about 3 to about 250 microns.

67. The barrier of claim 66, in which said film is substantially insoluble in water having a temperature less than about 50 degrees C.

68. The barrier of claim 48, in which said barrier includes a sixth layer which comprises a continuous film of a poly(vinyl alcohol), in which:

said film is not microporous in that it is substantially free of voids which connect the two surfaces of said film; and said film has an average thickness of from about 3 to about 250 microns.

69. The barrier of claim 68, in which said film is substantially insoluble in water having a temperature less than about 50 degrees C.

70. The barrier of claim 49, in which said barrier includes a sixth layer which comprises a continuous film of a poly(vinyl alcohol), in which:

said film is not microporous in that it is substantially free of voids which connect the two surfaces of said film; and said film has an average thickness of from about 3 to about 250 microns.

71. The barrier of claim 70, in which said film is substantially insoluble in water having a temperature less than about 50 degrees C.

72. A disposable diaper having as an outer cover the barrier of claim 1.

73. A disposable diaper having as an outer cover the barrier of claim 7.

74. A disposable diaper having as an outer cover the barrier of claim 17.

75. A disposable diaper having as an outer cover the barrier of claim 25.

76. A disposable diaper having as an outer cover the barrier of claim 42.

77. A disposable diaper having as an outer cover the barrier of claim 45.

78. A disposable diaper having as an outer cover the barrier of claim 48.

79. A disposable diaper having as an outer cover the barrier of claim 49.

80. A disposable diaper having as an outer cover the barrier of claim 50.

81. A disposable diaper having as an outer cover the barrier of claim 53.

82. A disposable diaper having as an outer cover the barrier of claim 57.

83. A disposable diaper having as an outer cover the barrier of claim 61.

84. A disposable diaper having as an outer cover the barrier of claim 64.

85. A disposable incontinent pad having as an outer cover the barrier of claim 1.

86. A disposable incontinent pad having as an outer cover the barrier of claim 7.

87. A disposable incontinent pad having as an outer cover the barrier of claim 17.

88. A disposable incontinent pad having as an outer cover the barrier of claim 25.

89. A disposable incontinent pad having as an outer cover the barrier of claim 42.

90. A disposable incontinent pad having as an outer cover the barrier of claim 45.

91. A disposable incontinent pad having as an outer cover the barrier of claim 48.

92. A disposable incontinent pad having as an outer cover the barrier of claim 49.

93. A disposable incontinent pad having as an outer cover the barrier of claim 50.

94. A disposable incontinent pad having as an outer cover the barrier of claim 53.

95. A disposable incontinent pad having as an outer cover the barrier of claim 57.

96. A disposable incontinent pad having as an outer cover the barrier of claim 61.

97. A disposable incontinent pad having as an outer cover the barrier of claim 64.

* * * * *

UNITED STATES PATENT AND TRADEMARK OFFICE
CERTIFICATE OF CORRECTION

PATENT NO. : 4,828,556

DATED : May 9, 1989

INVENTOR(S) : Ralph V. Braun, et al

It is certified that error appears in the above-identified patent and that said Letters Patent is hereby corrected as shown below:

In the abstract - "37 degrees about fifty percent relative humidity of from about 100 to Celsius and about 5,000 $g/m^2/24$ hour and is impermeable to 0.9 percent by weight saline solution at about 21 degrees C" should read --37 degrees Celsius and about fifty percent relative humidity of from about 100 to about 5,000 $g/m^2/24$ hour and is impermeable to 0.9 percent by weight saline solution at about 21 degrees C.--

Signed and Sealed this

Eighteenth Day of August, 1992

Attest:

DOUGLAS B. COMER

Attesting Officer

Acting Commissioner of Patents and Trademarks